(12) United States Patent
Paul

(10) Patent No.: US 6,830,557 B2
(45) Date of Patent: Dec. 14, 2004

(54) LIQUID FOAMING SOAP COMPOSITIONS AND DISPENSING SYSTEM THEREFOR

(76) Inventor: Leonard Paul, 13 Stuart Dr., Bloomfield, CT (US) 06002

(*) Notice: Subject to any disclaimer, the term of this patent is extended or adjusted under 35 U.S.C. 154(b) by 96 days.

(21) Appl. No.: 10/090,064

(22) Filed: Mar. 1, 2002

(65) Prior Publication Data

US 2002/0177534 A1 Nov. 28, 2002

Related U.S. Application Data

(63) Continuation-in-part of application No. 09/783,060, filed on Feb. 14, 2001, now Pat. No. 6,555,508.
(60) Provisional application No. 60/183,307, filed on Feb. 17, 2000.

(51) Int. Cl.[7] .............................................. A61M 5/178
(52) U.S. Cl. ........................ 604/37; 604/153; 604/275
(58) Field of Search ................................. 604/132, 153, 604/265, 408, 403, 19, 27, 36, 37, 39, 11, 264, 275, 279; 128/830; 424/422, 430, 44, 45, 47, 400, 401; 510/131, 137, 427; 514/945, 967

(56) References Cited

U.S. PATENT DOCUMENTS

| | | | |
|---|---|---|---|
| 3,682,176 A * 8/1972 | Kelsen | 604/150 |
| 3,771,523 A * 11/1973 | Zanca | 604/212 |
| 3,905,370 A * 9/1975 | Lazdowski | 604/200 |
| 3,948,260 A * 4/1976 | Whipperman et al. | 604/212 |
| 3,968,797 A * 7/1976 | Packer et al. | 604/215 |
| 3,993,070 A * 11/1976 | Sneider | 604/132 |
| 4,061,144 A * 12/1977 | Strickman et al. | 604/87 |
| 4,068,663 A * 1/1978 | D'Alessandro | 604/200 |
| 4,157,093 A * 6/1979 | Brodsky | 604/147 |
| 4,159,718 A * 7/1979 | Bower | 604/212 |
| 4,167,186 A * 9/1979 | Pick et al. | 604/212 |
| 4,168,032 A * 9/1979 | Sneider | 239/327 |
| 4,180,072 A * 12/1979 | Sneider | 604/32 |
| 4,184,974 A * 1/1980 | Van Leuven | 424/618 |
| 4,200,097 A * 4/1980 | Hobbs et al. | 604/213 |
| 4,223,814 A * 9/1980 | Sneider | 222/565 |
| 4,225,062 A * 9/1980 | Sneider | 222/211 |
| 4,230,111 A * 10/1980 | Piazza et al. | 604/518 |
| 4,324,242 A * 4/1982 | Cross | 604/213 |
| 4,392,492 A * 7/1983 | Pick | 604/82 |
| 4,405,321 A * 9/1983 | Budoff | 604/212 |
| 4,427,012 A * 1/1984 | Miller | 600/431 |
| 4,453,935 A * 6/1984 | Newton | 604/197 |
| 4,519,794 A * 5/1985 | Sneider | 604/212 |
| 4,526,751 A * 7/1985 | Gartner | 424/78.25 |
| 4,894,053 A * 1/1990 | Reddick | 604/85 |
| 4,964,852 A * 10/1990 | Dunning et al. | 604/75 |
| 5,102,387 A * 4/1992 | Jorde | 604/39 |
| 5,304,116 A * 4/1994 | Cornelius | 604/39 |
| 5,314,917 A * 5/1994 | Michaels et al. | 514/556 |
| 5,547,985 A * 8/1996 | Brown-Skrobot et al. | 514/546 |
| 5,853,767 A * 12/1998 | Melman | 424/659 |
| 6,113,580 A * 9/2000 | Dolisi | 604/268 |
| 6,162,202 A * 12/2000 | Sicurelli et al. | 604/272 |
| 6,293,928 B1 * 9/2001 | Fasani | 604/279 |
| 6,379,341 B1 * 4/2002 | Cho | 604/279 |

OTHER PUBLICATIONS www.bulkfoods.com/citric_acid.htm.*

* cited by examiner

Primary Examiner—Anhtuan T. Nguyen
(74) Attorney, Agent, or Firm—Melvin I. Stoltz

(57) ABSTRACT

By providing a mixture of surfactants and water, with the water content ranging between bout 40% and 95% by weight based upon the weight of the entire composition, a unique, improved, liquid based foaming soap formulation is realized which is useable for a wide variety of applications, including wet shaving and dry shaving. In the preferred embodiment, the improved liquid based foaming soap formulations incorporate one or more therapeutic active in sufficient quantities to assure its efficacy. As a result, the formulation is useable for a wide variety of medical applications for preventing, treating, or reducing the spread or transmission of bacteria, virus, infections, and the like.

13 Claims, 4 Drawing Sheets

LIQUID FOAMING SOAP COMPOSITIONS AND DISPENSING SYSTEM THEREFOR

RELATED APPLICATIONS

This application is a continuation-in-part of U.S. patent application Ser. No. 09/783,060, filed Feb. 14, 2001, now U.S. Pat. No. 6,555,508 entitled LIQUID FOAMING SOAP COMPOSITIONS which is related to U.S. Provisional Patent Application Ser. No. 60/183,307, filed Feb. 17, 2000 entitled ALL NATURAL, LIQUID FOAMING SOAP.

TECHNICAL FIELD

This invention relates to liquid soap formulations constructed for being dispensed as a foam product and, more particularly, to improved liquid formulations capable of being dispensed as a foam product for use in a wide variety of alternate applications, including for washing, shaving and use for medicinal or medical purposes.

BACKGROUND ART

Recently, the use of liquid soap has become extremely popular, with the ease and convenience provided by such products being appreciated by many individuals. However, in spite of the popularity of liquid soap, no widely useable, multi-purpose, effective liquid soap product has been developed which is capable of being dispensed as a foam mousse product to provide consumers with the substantially increased benefits inherent in a foam mousse and be useable for shaving and medical applications.

By providing an improved liquid soap formulation which are capable of being dispensed from a desired container as a foam mousse, consumers enjoy a wide variety of substantially enhanced benefits. In using any soap product, whether liquid or solid, the consumer is required to place a desired amount of the soap product in one's hands or on the area to be washed, and then vigorously rub the soap product in the hands or target site in order to develop a lather or foam, in order to achieve the desired cleaning. However, by dispensing the improved liquid soap product as a foam mousse directly from the container, ease of application and use of the product is enhanced.

A further benefit achieved from dispensing liquid soap as a foam mousse is a substantial reduction in the quantity of the product that must be dispensed at any particular time for any desired purpose. The foam mousse is produced by intermixing air into the soap formulations to produce the foam mousse product being dispensed. As a result, substantially less product is consumed at any particular time, thereby saving the consumer a substantial expense by controlling the amount of product being dispensed and thereby preventing unwanted wasting of product.

Another area in which consumer needs and desires have not been satisfied is in the area of shaving for both men and women. Although various shaving creams and foams have been created in attempting to provide a smooth, comfortable shave to men and women, manufacturers have typically resorted to producing shaving foams which rely upon aerosols or other foam producing gases.

Although these typical prior art products produce foams of various thicknesses and densities, these prior art products are incapable of achieving a product which is completely devoid of aerosols or other foaming agents or ingredients. Furthermore, such prior art products are bulky and require large containers or dispensers, as well as special pressurized gas holding systems, in order to accommodate the required aerosols for producing the foam.

Another area in which no effective prior art products have been developed is the medical area wherein numerous applications for a foam soap product exist with no solution being provided. Furthermore, in most of these areas, medicinal or therapeutic ingredients incorporated into the foam soap product would greatly enhance their use. However, no prior art product has been made which is capable of meeting this long-felt need. Some specific uses for a product of this nature are diseases and irritations in the vagina and/or the rectum where numerous problems exist that have been largely ignored. Although a long felt need has existed in these areas for safe and effective products, no prior art product has been achieved which is readily available and highly effective in treating or eliminating such diseases and problems.

Therefore, it is a principal object of the present invention to provide a multi-purpose, highly effective, liquid foam soap delivery system which is capable of being used in a wide variety of alternate product formulations and delivery systems.

A further object of the present invention is to provide a multi-purpose, highly effective, liquid foam soap delivery system having the characteristic features described above, which is capable of being dispensed from non-aerosol containers and produces a thick, rich, dense, foam mousse.

A further object of the present invention is to provide a multi-purpose, highly effective, liquid foam soap delivery system having the characteristic features described above, which incorporates an effective amount of a medical or medicinal ingredient for further enhancing the use and application of the present invention in a wide variety of alternate purposes.

Other and more specific objects will in part be obvious and will in part appear hereinafter.

THE DRAWINGS

For a fuller understanding of the nature and objects of the invention, reference should be had to the following detailed description taken in connection with the accompanying drawings, in which.

DETAILED DISCLOSURE

Figure 1:
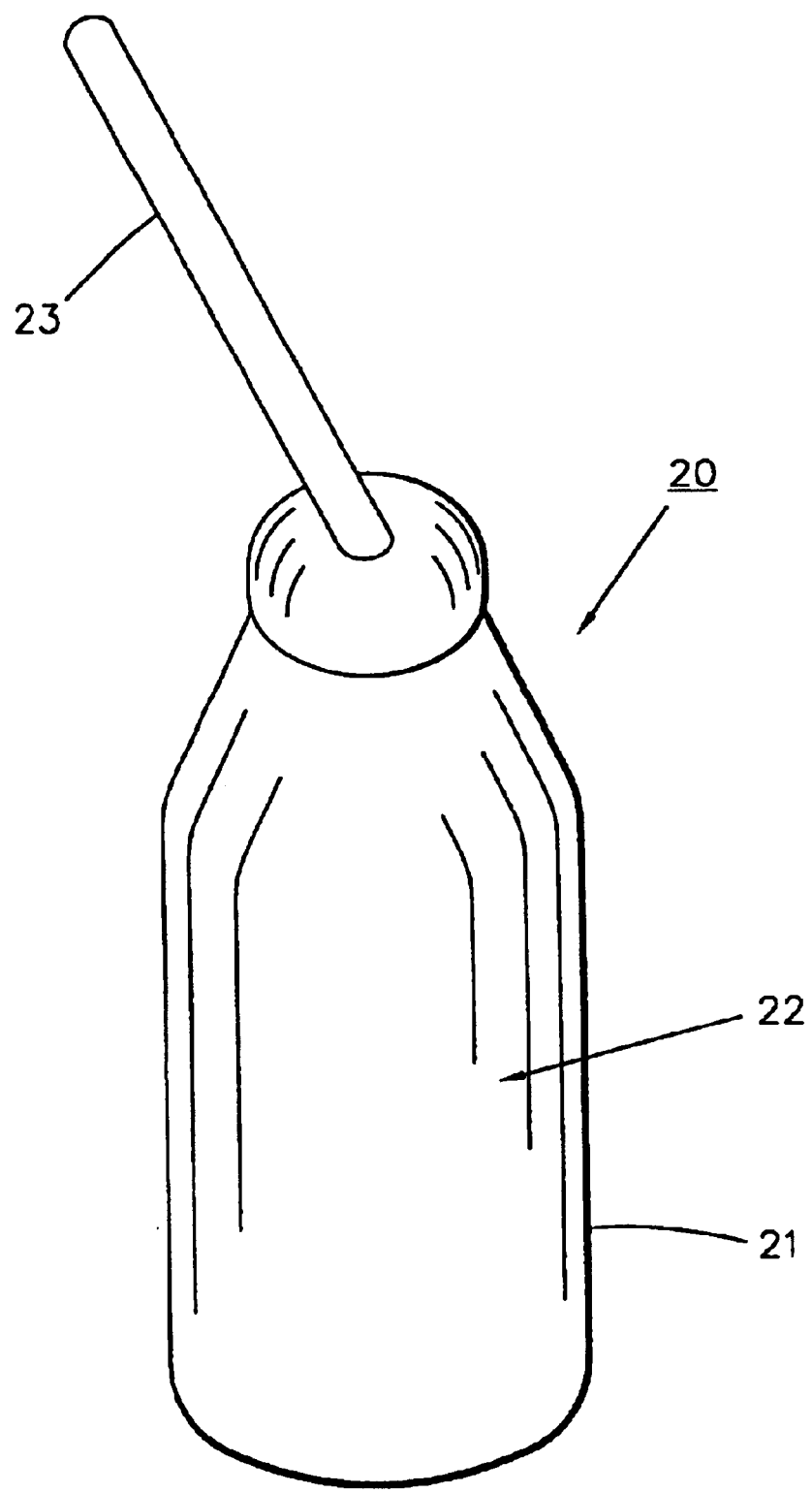
FIG. 1 is a perspective view of one embodiment of a delivery system incorporating a unique nozzle/cannula of the present invention.

By employing the present invention, all of the difficulties and drawbacks of the prior art have been overcome, and a highly effective, multi-purpose, universally applicable improved liquid based foam soap delivery system is achieved. In addition to attaining a universally useable, liquid based foam soap product, the present invention achieves an improved liquid based foam soap system that can be employed for all normal washing, as well as for shaving and for use as a device in treating a wide variety of medical conditions and problems.

The principal feature of the present invention is the attainment of an improved liquid based soap formulation which is capable of being employed with and dispensed from non-aerosol, foam-producing containers in a consistent and repeatable manner. Typically, conventional liquid soap formulations are incapable of repeatedly passing through the foam producing dispensing heads associated with foam containers/dispensers. Due to the inherent nature of conventional liquid soap, the fine mesh screens employed with foam heads are quickly clogged, preventing the effective, reliable use of conventional liquid soap in this manner.

With the present invention, a unique improved liquid soap formulation is realized which eliminates the prior art inabilities and provides a formulation which is effectively dispensed from foam producing dispensing heads in a consistent, reliable and repeatable manner, free from clogging failures. In accordance with the present invention, the principal ingredients are a mixture of surfactants, which inherently possess foam enhancing or foam producing qualities, and water with the quantity of water employed representing a critical factor. In order to achieve a formulation which is capable of being dispensed as a foam mousse, the total water employed must range between about 40% and 80% by weight of the total weight of the entire composition.

An additional ingredient which is preferably incorporated into the liquid foaming soap formulations of the present invention comprises one or more therapeutic agents. As is more fully detailed below, by incorporating a therapeutic agent, the present invention achieves a unique, universally employable, foam mousse product which is capable of being used in a wide variety of alternate applications for a wide variety of alternate purposes. In this regard, the presence of a therapeutic agent in the liquid foam soap formulation substantially enhances the usability and applicability of the liquid foam soap product, while also providing substantially enhanced beneficial results in areas where beneficial results have not been attainable.

In accordance with the present invention, it has been found that the quantity of the surfactants employed in the composition preferably ranges between about 5% and 70% by weight based upon the total weight of the entire composition.

The final ingredient incorporated into the improved liquid based foaming soap composition of the present invention is one or more therapeutic agents, used to achieve a desired, targeted or multi-functional result. In employing a therapeutic agent, the effective amount needed to achieve the desired result is employed.

In Table I, the overall composition discussed above is fully detailed. This composition represents the preferred formulation for achieving the goals of the present invention.

TABLE I

Liquid Foaming Soap Composition

| Ingredient | % by Weight |
| --- | --- |
| Mixture of Surfactants | 5–70 |
| Therapeutic Agent | Effective Amount |
| Water | 40–95 |
| pH adjusting agent | As needed |

In carrying out the teaching of the present invention, it has been found that one or more surfactants are preferably employed, with the surfactants being selected from the group consisting of polysorbate 20, cocoamide DEA, polysorbate 60, polysorbate 80, ammonium or alkaline salts of sulfated aliphatic alcohols, ammonium or alkaline salts of sulfated aliphatic ethoxylated alcohols, cocoamido derivatives and ethoxylated aliphatic phenolics.

By employing formulations made in accordance with the foregoing teaching, it has been found that a highly effective, multi-purpose liquid based foaming soap product is achieved. One of the principal features of this formulation is that the pH resulting from this composition is relatively mild for most uses. However, if desired, the pH is easily adjusted to range between about 7.0 and 7.6. As a result, virtual neutrality is attainable and the liquid foaming soap product is comfortable for virtually any use or application.

In the preferred embodiment, the improved, multi-purpose liquid foaming soap formulation of the present invention comprises an effective amount of a therapeutic agent. Typically, the therapeutic agent comprises one or more selected from the group consisting of antiseptic agents, anti-bacterial agents, anti-microbial agents, anti-viral agents, medicines, anti-inflammatory agents, anesthetics, analgesics, and anti-itch agents. Depending upon the particular use desired, one or more therapeutic agents are added to the composition in order to provide the desired enhanced result.

Although the therapeutic agent employed in the liquid foaming soap composition of the present invention may be selected from a broad category of therapeutic compounds which provide the desired functions detailed above, the following agents comprise a representative sample of the type of agents that has been found to be highly effective in achieving the goals of the present invention. This sample of therapeutic agents comprises one or more selected from the group consisting of triclosan, spirulina, calcium spiruline, nonoxynol-9, benzocaine, lidocaine, silver nitrate solutions, lidocaine-hydrochloride, iodine, povodone-iodine, and hot water solutions of spirulan. As detailed below, each of these therapeutic agents provides a particular target area or desirable function for enabling the improved liquid foaming soap composition of the present invention to be used to attain results previously thought to be unattainable.

One product area which typifies a composition of the present invention is the creation of an antiseptic, anti-bacterial, or anti-microbial liquid based foaming soap for general, everyday use, and/or for application wherein an antiseptic or anti-bacterial soap is desired. In order to attain a product of this nature, it has been found that by incorporating triclosan as the therapeutic agent, a highly effective, anti-bacterial, antiseptic and/or anti-microbial liquid based foaming soap product is realized. In addition, by adding nonoxynol-9 as the therapeutic agent, an anti-viral formation is attained to be used for medicinal or medical purposes in hospitals, nursing homes, and elderly housing for use when water is not available, or for general cleanliness. Furthermore, it has also been found that the use of an aqueous solution of silver nitrate as the therapeutic agent creates a formulation which can be employed for treating burn victims.

In Table II, a preferred formulation for using triclosan in the liquid foaming soap product of the present invention is detailed, while Table III provides a more detailed formulation, with the specific ingredients for all functions being provided. In formulating this product, the established effective amount of triclosan ranges between about 0.2% and 2.0% by weight based upon the total weight of the composition.

TABLE II

Anti-Bacterial/Antiseptic Foaming Soap

| Ingredient | % by Weight |
|---|---|
| Mixtures of Surfactants | 5–70 |
| Triclosan | 0.2–2.0 |
| Water | 40–95 |
| pH Adjusting Agent | As needed |

TABLE III

Anti-Bacterial/Antiseptic Foaming Soap

| Ingredient | % by Weight |
|---|---|
| Polysorbate 20 | 5–30 |
| Cocoamide DEA | 3–10 |
| Ammonium Lauryl Sulfate | 25–40 |
| Triclosan | 0.2–2.0 |
| Water | 40–80 |
| pH Adjusting Agent | (q.s. for pH of 6.5–8.0) |

In achieving an effective, useable and desirable anti-bacterial/antiseptic liquid foaming soap product which employs triclosan, it has been found that polysorbate 20 is preferably employed as a surfactant in order to allow the triclosan to be dissolved in the aqueous solution. Since triclosan is not water soluble, an agent is required to dissolve the triclosan into the solution. Although polysorbate 20 is preferred for this purpose, another equally effective agent may also be used.

In addition, it has also been discovered that the quantity of cocoamide DEA employed in the composition preferably ranges between about 3% and 30% of the quantity employed for the ammonium lauryl sulfate. By employing these parameters, a highly effective, multi-purpose, antiseptic/anti-bacterial liquid foaming soap product is achieved.

In addition to achieving an effective antiseptic/anti-bacterial liquid foaming soap composition, the foregoing composition also possesses a pH of about 6.5 to 8.0. This result is attained by employing the ingredients such as citric acid or equivalent, in the quantities detailed above, along with a small quantity of one or more pH adjusting agents which are well known to those skilled in this art.

Other areas which greatly benefit from the attainment of a liquid based foaming soap composition which incorporates a therapeutic agent are found in a wide variety of medical or medicinal applications. In this regard, various diseases which are caused by viruses have been virtually ignored by prior art products due to the inability of these prior art products to deliver an effective anti-microbial or anti-viral composition directly to the problem site.

The two areas where problems had continuously plagued the medical field and have gone unsolved are found with the diseases and/or irritations which affect the vagina and/or the rectum such as chlamydia or gonorrhea. However, by employing the present invention, these problem areas are quickly and easily resolved.

It has been found that by incorporating an effective amount of an anti-bacterial, anti-microbial, anti-viral, anti-itch, antiseptic, anti-inflammatory, anesthetic, and or analgesic therapeutic agent in the liquid based foaming soap composition of the present invention, a safe and highly effective treatment system is realized for treating various anatomical problems, particularly vaginal and rectal diseases and irritations. In this regard, therapeutic agents such as triclosan, nonoxynol-9, octoxynol-9, silver nanocrystals, and other equivalent anti-viral or anti-bacterial compositions, can be employed in the liquid foaming soap formulations of the present invention to produce a resulting product capable of resolving problems that have been unresolved for long time periods.

By employing the compositions detailed above for attaining an anti-bacterial, anti-viral, and/or anti-microbial liquid foaming soap product, a safe, and effective delivery system is realized for enabling any individual or healthcare provider to quickly, easily, and conveniently apply a soap product directly to areas which are otherwise incapable of being easily accessed, with complete assurance that both cleaning and anti-viral medication is simultaneously delivered precisely to the site where needed. As a result, by employing the present invention, areas of the body are capable of been effectively treated where presently no effective treatment is available.

It is our intent to take advantage of the well-known phenomena caused by surface active agents on cohesion and surface tension to make use of the foam mousse product as a medical device when used with a formulation composed of an anti-bacterial or anti-viral drug and in some cases a combination of the two. The anti-bacterial foam soap composition that includes Triclosan in the formulation has been produced and has been found to help eliminate bladder infection in women caused by improper or negligent habits when using the toilet.

The pH of the anti-bacterial soap formula had to be lowered to 7 in order to accommodate any tender skin areas. A small amount of the foam mousse interspersed with triclosan or other anti-bacterial, or the anti-viral agent, such as nonoxynol-9, when applied onto toilet tissue to the rectum and vaginal area, helps in reducing the chance for this type of bladder infection. The foam mousse dries rapidly and the film of soap is gentle and does not cause any irritation. The film can be removed by simply wetting toilet tissue after 30 seconds if necessary. The foam mousse is packagable in a pocketbook size three ounce foamer.

There are many other areas in which the anti-bacterial/anti-viral foam soap compositions of this invention can be used as a medical device such as within a hospital setting, the workplace, in the home, the armed services, or any other event that an open wound of any size is a possibility. In a hospital or surgical setting, protection from viral or bacterial infections is a priority. With the use of a foamer and the proper antiseptic foam, a protective skin is produced that should protect the cells surrounding the wound from infection. It follows that the same protective event will follow in any location where an open wound or cut has happened.

As a prophylactic, the foamer when used by either the female and the male, should enhance protection against the spread of diseases. The female sprays nonoxynol-9, or other proven anti-AID's drug, deep into the vagina or rectum in the case of males. The second barrier would be set up by the male wetting the penis with water and then using the same foam spread around the penis. The formulation is slippery enough to act as a lubricant to enhance the ease of the sexual act.

In a further area, the foam mousse is well suited for burn patients, since it lays down a layer of medicant easily and without irritation. Povidone iodine complex (10% active) a silver nitrate solution (0.5% active) and silver nanocrystals (0.1% solution) are excellent antiseptics for burn patients. Povidone iodine, silver nitrate, and silver nanocrystals are water based solutions to be sprayed or placed over the affected area without any rubbing. By employing the present invention, the active therapeutic agent is slowly released onto the skin, providing or assisting in the healing process. As with all burn patients, bandages should not be placed over the affected area.

In order to attain the desired foam mousse from the liquid foaming soap composition of the present invention, non-aerosol, unpressurized, foam delivery dispensers known in the art are employed. These dispensers typically comprise a movable, finger-operated dispensing head or cap mounted to a container in which the improved liquid soap composition of the present invention is retained. The movable, finger operated dispensing head/cap is constructed to draw the liquid foaming soap composition from the container into the cap and force the composition through various screens while intermixing air therewith to produce a dispensed product which comprises a foam mousse.

In an alternate configuration, the prior art foam delivery dispenser comprises a soft pliable bottle in combination with a dispensing cap/head structure which allows the user to squeeze the soft pliable bottle to force the composition in the container to pass through the cap and deliver the desired foam mousse product. Regardless of which structure is employed, the resulting foam mousse product is substantially equivalent and can be employed with equal efficacy in the present invention.

In most applications employing the present invention, the liquid foaming soap composition defined herein is retained in a container incorporating the movable, finger-operated dispensing head/cap. In this way, the desired foam mousse product is quickly and easily dispensed into one's hand for use and application directly to the hands or to any other desired site or location.

Alternatively, in those applications where delivery directly into cavities, such as the vagina or the rectum are desired, the squeeze bottle construction is preferred. In addition, a soft, pliable, elongated tube or nozzle is mounted to the cap, to enable the foam mousse product to be delivered directly in the particular cavity at the precise location of the inflammation or virus being treated. In this way, direct application is realized with ease and efficiency.

By referring to FIGS. 1–4, along with the following detailed discussion, two alternate embodiments for a delivery system for the present invention are fully detailed. In particular, FIGS. 1–4 and the following detailed discussion focused upon two preferred embodiments for delivering the compositions of the present invention directly into cavities, such as the vagina or rectum as discussed above.

Figure 4:
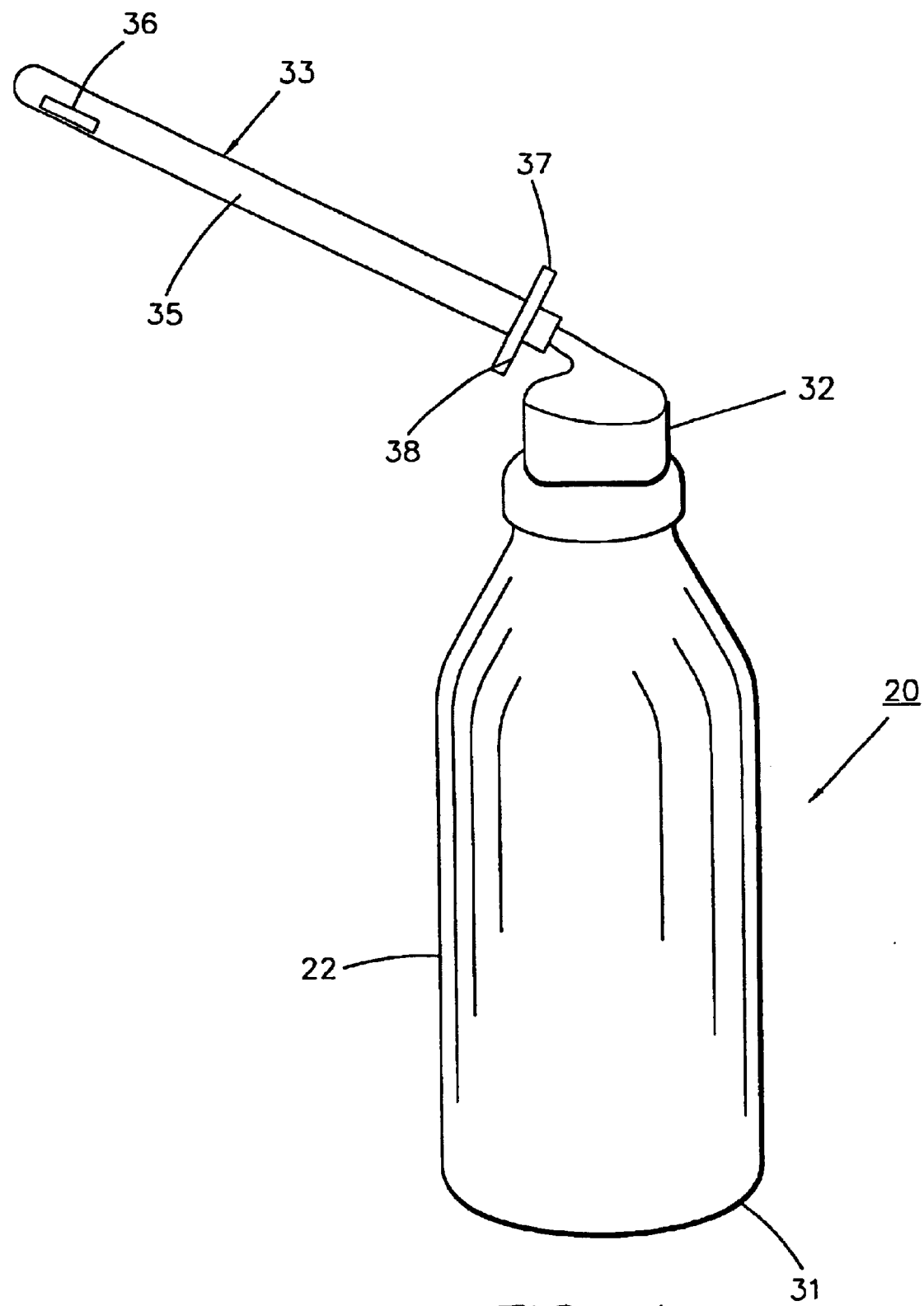
FIG. 4 is a perspective view of a second embodiment of a delivery system incorporating an alternately constructed nozzle/cannula.

In FIGS. 1 and 4, two alternate delivery system constructions are depicted, both of which can be employed with equal efficacy. In the embodiment depicted in FIG. 1, delivery system 20 comprises squeeze bottle 21, which contains the desired formulation 22, made in accordance with the present invention. In addition, delivery nozzle or cannula 23 is mounted to bottle 21 in order to deliver the desired formulation directly to the precise location where formulation 22 is desired for optimum efficacy.

Figure 2:
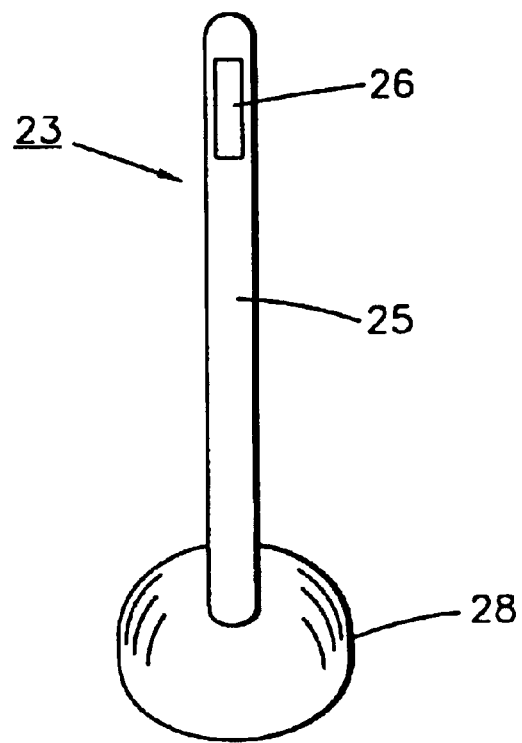
FIG. 2 is a front perspective view of the nozzle/cannula shown in FIG. 1.
Figure 3:
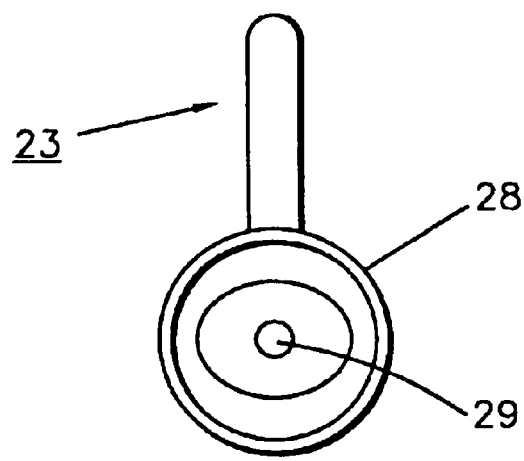
FIG. 3 is a bottom perspective view of the nozzle/cannula shown in FIG. 1.

In this regard, delivery nozzle/cannula 23, which is more fully depicted in FIGS. 2 and 3, comprises a uniquely constructed, elongated tube portion 25 which is specifically configured for insertion into desired human cavities, such as the vagina or the rectum. In this regard, tube portion 25 comprises a precise overall length which assures complete insertion of tube portion 25 in the desired orifice, without injuring the surrounding soft tissue. In addition, tube portion 25 is constructed with maximum flexibility in order to provide ease of use.

Generally, this length preferably comprises between about 2 inches and 3.5 inches. In addition, the distal end of tube portion 25 comprises apertures 26 formed therein in order to deliver the desired formulation to the precisely desired location. In this way, a safe, effective, and reliable delivery system is realized.

In order to be certain that over-insertion of delivery nozzle/cannula 23 into a human is avoided, delivery nozzle/cannula 23 comprises any enlarged cap 28 formed at the proximal end of tube portion 25. By employing enlarged cap 28, a positive stop surface is provided, preventing accidental over-insertion of tube portion 25. In addition, this construction also prevents unwanted dislodgment of nozzle/cannula 23 and suction thereof into the cavity by the creation of a vacuum.

In addition, in the preferred embodiment, cap 28 comprises an interior threaded zone which is quickly and easily mounted to bottle 21 directly to threads formed thereon. In this way, delivery nozzle 23 is quickly mounted to bottle 21, after the desired composition 22 has been placed into bottle 21. As a result, the entire assembly is achieved both quickly and easily.

In accordance with the present invention, nozzle/cannula 23 may be molded with any desired length and diameter in order to satisfy the particular requirements of any desired application or use. In this regard, if required, the depth insertion guard can be eliminated.

Furthermore, in forming nozzle/cannula 23 of this invention, any bottle diameter, thread construction, or mounting system can be accommodated. In satisfying any such needs, nozzle/cannula 23 is molded with the desired configuration for achieving a particular construction or arrangement.

One common configuration found in the prior art for bottle 21 is the construction of bottle 21 with a flexible, thin-wall. By employing this type of bottle construction, a low-cost, extremely flexible bottle delivery system is realized. However, although bottles of this nature have been well received, due to their low cost and ease of use, control of the delivery pressure and the flow of the product through the delivery tube has been extremely difficult to properly regulate. As a result, either unsatisfactory flow control is produced or expensive valve constructions are required.

By employing the present invention, all of these difficulties and drawbacks have been completely eliminated, and an inexpensive product delivery system is realized, capable of providing complete control over the flow of formulation 22, without requiring expensive valve configurations. As best seen in FIG. 3, the present invention is constructed with tube portion 25 mounted in cap 28 with a small diameter aperture 29 communicating between the interior of bottle 21 and the open delivery channel formed in tube portion 25 through which composition 22 flows.

By controlling the diameter of aperture 29 to comprise a small diameter, consistent with the overall diameter of tube portion 25, complete control over the flow of product 22 through delivery tube 25 is automatically realized. By providing this construction, the requisite amount of back pressure is provided for enabling the user to effectively squeeze bottle 21 for delivery of product 22 through tube portion 25 in a consistent, efficient manner. Furthermore, by employing this construction, both ease of flow is attained as well as efficient delivery of product 22 through apertures 26.

In order to attain these highly desirable results, it has been found that tube portion 25 preferably comprises an outer diameter ranging between about 0.25 and 0.35 inches. Consistent with this overall outer diameter is the interior diameter of tube portion 25 which controls the dimension of aperture 29. In this regard, the preferred inside diameter of aperture 29 ranges between about 0.050 and 0.200 inches with a range of between about 0.080 and 0.156 being most desirable. By employing this construction, the desired flow characteristics and pressure control of squeeze bottle 21 are realized.

Furthermore, it has also been discovered that the delivery pressure is controlled by the size and number of apertures or slits 26 formed in delivery tube 25. Consequently, additional precise control over the performance of delivery system 20, as well as its delivery pressure, is realized by forming apertures/slits 26 in delivery tube 25 with a precise dimension as well as by controlling the number of apertures/slits 26 being employed. In this regard, nozzle/cannula 23 may be constructed with any desired thickness as well as with a smoothly curve, rounded end for comfort and ease, with a single aperture or slit 26 being formed in the rounded terminating end thereof.

In addition to employing the various product formulations 22 detailed herein for being dispensed by bottle 21 of delivery system 20 of FIG. 1, soft, flexible, readily compressible bottles 21 have typically been employed in the prior art for delivering douche products to individuals. It has been found that by employing delivery system 20 of FIG. 1 with a unique douche product formulated in accordance with this invention, a highly effective, therapeutic, and anti-viral treatment system is realized. In this regard, Table IV provides a preferred douche formulation which achieves both conventional cleaning and freshening, as well as providing therapeutic and anti-viral benefits.

TABLE IV

| Ingredient | Preferred %/Wgt | Range %/Wgt |
|---|---|---|
| Deionized Water | 88.65 | q.s. to 100% |
| Citric Acid Powder, USP | 0.05 | 0.01–0.08 |
| Nonoxynol-9, USP or Octoxylnol-9 | 1.00 | 1.00–5.00 |
| Glycerine, UPS | 10.00 | 8.0–12.00 |
| Povidone Iodine (#30/06) | 0.03 | 0.30–2.0 |
| Fragrance | As needed | As needed |

In formulating the douche product defined in Table IV, it is preferable to first add the deionized water to a standardized batch tank. Once the water extends over the mixing blades, moderate mixing should begin. Thereafter, each ingredient is added in the order provided in Table IV, and the formulation is mixed for 30 minute in order to assure complete intermixing. Once fully mixed, this formulation is added to bottle 21 to provide the desired therapeutic and anti-viral douche system.

In FIG. 4, an alternate delivery system 20 made in accordance with the present invention is depicted. In this embodiment, bottle 31 is employed with the desired formulation 22 contained therein. In addition, in order to dispense product 22 from container 31, a finger operated, non-aerosol, pump valve 32 is employed by being affixed to the portal of bottle 31. In accordance with the present invention, virtually any desired, finger operated, pressure producing pump valve 32 may be employed. However, it has been found that high-pressure pump valves provide optimum results.

In accordance with the present invention, the construction of this embodiment of delivery system 20 is completed by inserting nozzle/cannula member 33 into the exit portal of valve 32. As fully detailed below, by employing this alternate embodiment, any desired formulation 22 is delivered precisely to the location where optimum efficacy is achieved.

In this embodiment, nozzle/cannula member 33 comprises an elongated tube portion 35 which is specifically configured for insertion into the desired human cavity, such as the vagina or the rectum. As with the embodiment detailed above, tube portion 35 comprises the precise overall length which assures complete insertion of tube portion 35 in the desired orifice or cavity, without injuring the surrounding soft tissue. As detailed above, this overall length typically comprises between about 2 inches and 3.5 inches.

As with the embodiment detailed above, the distal end of tube portion 35 comprises apertures 36 formed therein in order to enable the desired formulation to be uniformly dispensed precisely at the desired location. As a result, a safe, effective, and reliable delivery system is attained.

In this embodiment, in order to assure that over-insertion of nozzle/cannula member 33 into a human is avoided, nozzle/cannula member 33 incorporates an enlarged flange 37 formed adjacent the proximal end thereof for providing a positive stop surface. By incorporating flange 37, nozzle/cannula member 33 is incapable of being inserted beyond the precisely desired overall length.

The construction of nozzle/cannula member 33 is completed by forming proximal end 38 thereof in a manner which provides ease of engagement and securement in the portal of pump valve 32. By constructing proximal end 38 with an overall diameter that assures secure, frictional interengagement thereof in the portal of pump valve 32, an easily assembled, dependable and reliable delivery system 20 is realized. As is evident from this foregoing disclosure, the desired formulation 22 is easily dispensed at the precisely desired location in the human body by merely inserting nozzle/cannula member 33 into the desired cavity and then pressing pump valve 32 in order to dispense product formulation 22 to the precisely desired site.

As is evident from the foregoing detailed discussion, two alternate constructions for a highly effective and reliable product delivery system are attained by the present invention. By employing either of these alternate constructions, any desired formulation can be delivered by pressure to a precise interior location in the human body with ease and simplicity. Furthermore, both of these alternate embodiments enable any desired formulation to be delivered in a safe and effective manner to the precise sites or location where optimum beneficial results are attained. If desired, dip tubes can be employed with these embodiments for assisting in dispensing the desired formulation. In addition, both embodiments may be constructed with the bottles being re-fillable in order to achieve substantial economical benefits.

In addition to delivery of product formulations 22 under pressure, a further alternate method often employed is gravity feed. Although the nozzle/cannula constructions detailed above have been found to be equally effective in delivering any desired product using a gravity feed method, it has been found desirable to include a check valve or one-way valve formed in combination with the nozzle/cannula, in order to assure the delivery of the product to the desired location, without any chance of backwash or back-flow being produced. As a result, a check valve or one-way valve construction is preferably incorporated into the nozzle/cannula of the present invention for gravity feed systems, particularly when using the present invention in the rectal area. In addition, if desired, a similar check valve or one-way valve can also be incorporated into the pressure delivery nozzle/cannula constructions detailed above in order to assure similar backflow or backwash problems are completely avoided.

Figure 5:
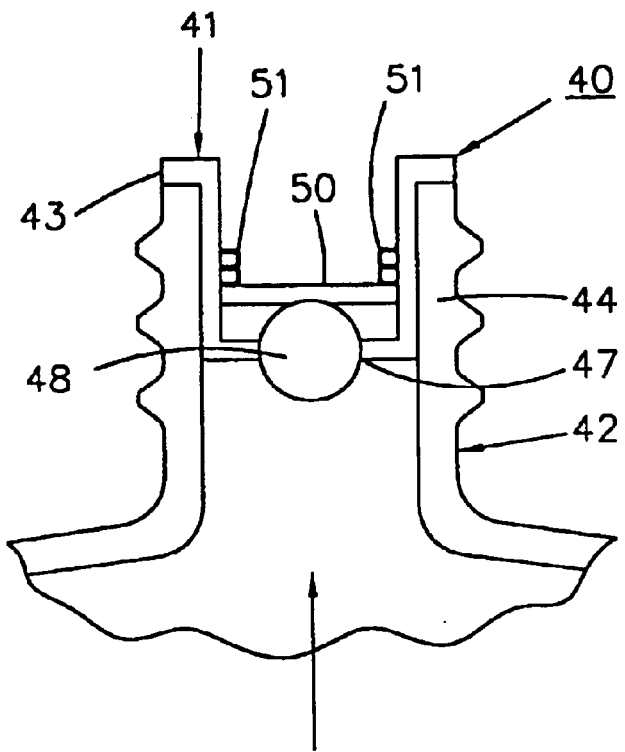
FIG. 5 is a cross-sectional side elevation view, partially broken away, depicting a check valve mounted in a bottle.
Figure 6:
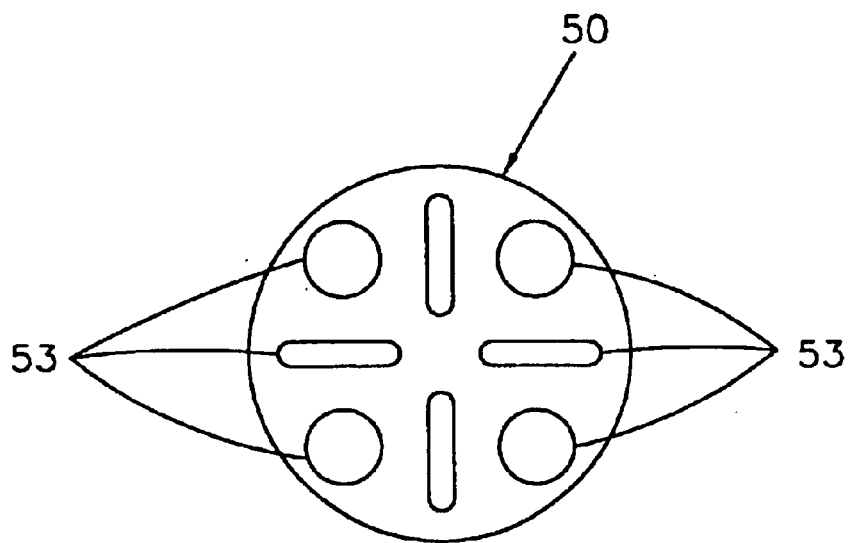
FIG. 6 is a top plan view of a disk member forming a component of the check valve of FIG. 5.

By referring to FIGS. 5 and 6, along with the following detailed discussion, a preferred construction for check valve 40 can best be understood. In this preferred embodiment, check valve 40 comprises cup member 41 which is inserted into neck or portal 44 of bottle 42. By forming cup member 41 with a radially extending flange 43 which peripherally surrounds the opened end thereof, cup member 41 is quickly and easily inserted into neck/portal 44 and securely retained in position. In addition, in order to complete the secure retention and placement of check valve 40, a suitable cap is threaded onto neck/portal 44 of bottle 41, securing cup member 41 between the cap and bottle 42.

In order to provide the desired controlled flow of the product retained in bottle 42, check valve 40 incorporates an aperture 47 formed in the base of cup member 41 and spherical ball 48 constructed for movable engagement with aperture 47. This construction is completed by providing movable disk 50 which cooperates with spherical ball 48 and cup member 41. In the preferred construction, disk 50 is capable of limited, controlled, axial movement within cup member 41, with said axial movement being limited between contact with spherical ball 48 and retaining ribs or detents 51 formed on the inside wall of cup member 41.

As clearly shown in FIG. 6, disk 50 comprises a plurality of apertures or through holes 53 formed therein in order to enable the composition retained in bottle 42 to easily pass through disk 50. However, before any product retained in bottle 42 is capable of flowing through check valve 40, spherical ball 48 must be dislodged from aperture 47.

As is evident from the foregoing detailed discussion, whenever pressure is applied to bottle 42, or bottle 42 is inverted to cause gravity flow of the composition retained therein, spherical ball 48 is dislodged from aperture 47, enabling the composition retained in bottle 42 to flow through aperture 47, around ball 48, and through apertures or portals 53 formed in disk 50. The required movement of disk 50 which enables spherical ball 48 to be dislodged from aperture 47 is provided by the limited axial movement of disk 50 within cup member 41 between ball 48 and ribs/detents 51.

In addition, whenever activation pressure is removed from bottle 41, or reverse flow is experienced from the delivery side of check valve 40, disk 50 returns to its original position, forcing spherical ball 48 into aperture 47. As a result, flow into bottle 42 from the delivery source is stopped and contamination of the composition in bottle 41 is prevented. In this way, all of the attributes sought to be achieved in the delivery of a composition in accordance with the present invention are realized, either pre or post coitus.

A further area in which it has been found that the present invention is highly effective in providing a therapeutic treatment system, which presently does not exist, is in treating or reducing the transmission of viral diseases, such as AIDS, herpes, and chlamydia. By employing the present invention with a suitable therapeutic agent incorporated therein, a prophylactic treatment system is realized for helping to prevent the transmission of these viral diseases.

In order to attain an effective anti-viral treatment system employing the liquid foaming soap composition of the present invention, it has been found that the therapeutic agent incorporated into the composition is preferably selected from the group consisting of spirulina, calcium-spirulan, nonoxynol-9, octoxynol-9, hot water solution of spirulan, and povidone iodine or iodine salt. These compounds, along with other compounds being developed having equal efficacy, can be employed in the present invention in order to provide the desired prophylactic results.

Recently, it has been found that these compounds are capable of inhibiting viral replication, while strengthening both the cellular and hormonal arms of the immune system, causing regression and inhibition of various diseases. As a result, these compounds, and their equivalents, provide effective therapeutic agents for being incorporated in the liquid foaming soap composition of the present invention in order to provide an easily used, highly effective medicinal delivery system for helping to reduce transmission of viral diseases such as AIDS, herpes, chlamydia and gonorrhea. In addition, by employing these formulations using the delivery system detailed above, a highly effective and easily employed product is realized.

Another area in which the present invention has proven to be highly effective is in the use of the liquid foamed soap product for shaving. In attempting to satisfy consumer demand for a wet or dry shaving cream which will provide a smooth, comfortable shave to both men and women, manufacturers have typically produced shaving foams which rely upon aerosols or other foam producing gases. Although these typical prior art products produce foams of various thicknesses and density, these prior art products have not been able to achieve a natural product, which is completely free from aerosols or other foaming agents or ingredients. Furthermore, such prior art products are bulky and require large containers or dispensers, as well as special pressurized gas holding systems, due to the use of aerosols for producing the foamed product.

By employing the liquid foaming soap formulation of the present invention, all of the prior art difficulties and drawbacks are eliminated and a natural, liquid foaming soap product is attained which is free of any aerosol or gaseous foaming member or foam producing agent/ingredient. Furthermore, in accordance with the present invention, the entire dispensing system comprises a small, compact, non-pressurized container, within which the liquid foaming soap formulation of the present invention is retained, along with a foam producing dispensing valve/head or cap.

In accordance with the present invention, a unique liquid foaming soap formulation is realized which provides a soap product capable of being dispensed as a foamed mousse, having the thickness and density required for providing a smooth comfortable shave for all beards, legs, underarms, and any other desired areas to be shaved. In addition, the formulations of the present invention may comprise all natural ingredients while enabling women to shave their legs without water.

Due to the thickness and density achieved by the foam mousse produced by the present invention, the shaving foam product of this invention retains its moisture while on the surface to be shaved. In addition, the shaving mousse of this invention produces an inherent low friction, gliding surface over which a razor comfortably passes while cutting the desired beard or hair fibers. In addition, it has been found that the shaving mousse substantially increases the ability of causing hair or whiskers to become erect, further enhancing and improving the closeness of the shave. As a result, shaving of any desired area is achieved with a high comfort level, while also assuring close cutting of all hair folicals. Furthermore, due to these highly desirable characteristics, even sensitive skin is able to enjoy a close and comfortable shave, virtually devoid of any irritation or discomfort.

Furthermore, in using the present invention with a dry shaver, only a small amount of the foam mousse product is employed to attain the desired results. Once a small quantity of mousses is spread over the face of the user, a close and comfortable shave is realized.

In order to attain the desirable and previously unrealized results provided by the present invention, the shaving mousse of the present invention is achieved by combining a low viscosity or liquified soap in combination with a suitable dispenser. In accordance with this invention, a conventional container is employed which incorporates a valve or dispensing cap capable of receiving the liquified soap, and delivering a foamed shaving mousse. In this way, all of the prior art inabilities are completely eliminated and a unique, compact, foam shaving formulation and delivery system is attained.

The invention accordingly comprises a composition of matter possessing the characteristics, properties, and the relation of constituents which will be exemplified in the compositions hereinafter described, and the scope of the invention will be indicated in the claims.

BEST MODE FOR CARRYING OUT THE INVENTION

By referring to the following detailed disclosure, various preferred constructions and formulations of the liquid foaming soap of the present invention, and the production of such compositions can best be understood. Although the following disclosure specifically details alternate formulations for the liquid foam soap compositions, as well as preferred methods for creating the compositions, alternate formulations and methods can be employed without departing from the scope of this invention. Consequently, it is to be understood that the following specific formulations and methods are provided for exemplary purposes and any alternate formulations and production methods coming within the scope of the present invention are intended to be encompassed therein.

In one preferred embodiment of the present invention, a multi-purpose, antiseptic, anti-bacterial, and/or anti-viral liquid foaming soap formulation capable of producing a thick, rich, moisture laden foam shaving mousse is attained.

By referring to Table V, the preferred, specific formulation for this multi-purpose, antiseptic, anti-bacterial, and/or anti-viral improved liquid foaming soap product is provided. Although these formulations may be varied, Table V provides the preferred, specific formulation for this multi-purpose product.

TABLE V

| Ingredient | % by Weight |
| --- | --- |
| Polysorbate 20 | 10 |
| Ammonium Lauryl Sulfate | 30 |
| Cocoamide DEA | 5 |
| Triclosan | 0.2 |
| Water | 54.8 |

In order to attain a thoroughly intermixed, substantially homogeneous, multi-purpose improved liquid foaming soap composition employing the ingredients defined in Table V, it has been found that a preferred mixing process be employed. In this regard, polysorbate 20 and triclosan are added to a first vessel, heated to about 65° C. and continuously mixed together until fully dissolved. In addition, ammonium lauryl sulfate and cocoamide DEA are intermixed in a second vessel and heated to about 65° C. These components are also intermixed until fully dissolved.

In the next process step, polysorbate 20-triclosan mixture is added to the ammonium lauryl sulfate and cocoamide DEA combination and the resulting composition is thoroughly mixed. Then, the water is added to the component mixture and the entire mixture is heated to a temperature of about 50° C. Once heated, thorough intermixing of all components is provided, and when completed, the resulting composition is allowed to cool to room temperature.

It has been found that the resulting composition produced by employing the foregoing process typically has a pH of about 8.4. In order to lower the pH to between about 6.5 and 8.0, a desired pH adjusting agent is employed. Typically, citric acid or mild H.L. is effectively used for this purpose.

By employing the process detailed above, or an equivalent process, a highly effective, multi-purpose, antiseptic, antibacterial, and/or antiviral liquid foaming soap composition is realized. As detailed above, the resulting composition is placed in a container which is then interconnected with a movable, finger operated foam dispensing cap/valve or a foam producing cap member which relies upon squeezing of the container for forcing the composition there through. Preferably, if this latter construction is employed, the foam producing cap member incorporates an elongated, soft, pliable, nozzle member mounted thereto for enabling the delivery of the foam product directly to any desired site or location, such as an internal site located within a body cavity.

It has been found that by employing the present invention, a highly desirable, multi-purpose, antiseptic, anti-bacterial, and/or anti-viral liquid based foam soap product is attained, which can be used for hand and body washing, wet or dry shaving, and a wide variety of medical or medicinal purposes. In addition, by substituting an effective amount of another therapeutic agent for the triclosan incorporated in the formulation detailed above, a highly desirable, easily employed, foam soap product is realized which is capable of delivering a particular, desired therapeutic agent to a specific location for treating a specific medical need.

As detailed above, exemplary of such a medical purpose is the reduction in the spreading or transmission of diseases such as AIDS, herpes, and chlamydia by employing an anti-viral agent such as nonoxynol-9, spirulines, calcium spiruline and hot water solutions or spirulan. Furthermore, a liquid-based foam soap formulation particularly suitable for assisting in the treatment of burn victims is realized by employing povidone-iodine or silver nitrate solutions as the therapeutic agent.

Although specific alternate formulations for compositions employing alternate therapeutic agents are not specifically provided herein, such alternate formulations are clearly within the teaching of the present invention by employing the formulations and production steps detailed above. As a result, the incorporation of virtually any therapeutic agent into the basic formulations of the present invention is clearly within the scope of this invention and is intended to be encompassed by the claims of this invention.

In addition, it has also been found that the formulation detailed above produces a rich, thick, moisture laden foam which is equally applicable for use in both wet and dry shaving. By employing the foam mousse produced by the compositions detailed above, a foam mousse product is realized which is easily spread on the skin surface for enabling the user to shave either long hair or short hair, by employing conventional wet or dry shaving systems, such as razor blades or electric shavers. As a result, a highly effective, multi-purpose, liquid based foam soap product is realized by the present invention.

In addition to the foregoing detailed formulations, it has also been found that a thick, rich, moisture laden foam shaving or mousse is attained by employing the overall teachings of the present invention, as detailed above, by using various other surfactants, foaming agents, and combined foaming agents/surfactants. In this regard, it has been found that a highly desirable foam shaving mousse is realized by intermixing stearic acid, coconut oil acids, purified water, and pH adjusting agents.

In the preferred construction of this embodiment, the stearic acid comprises between about 2% and 5% by weight based upon the weight of the entire composition, while the coconut oil acids comprise between about 20% and 30% by weight based upon the weight of the entire composition. The purified water and the pH adjusting agents with natural fragrances and preservatives forms the balance of the improved liquid soap formulation.

By employing these ingredients, an all-natural, liquid foaming soap product is attained which is capable of being employed to provide the desired thick, rich, moisture laden foam shaving mousse. It has also been found that the liquid foaming soap product of the present invention may be further enhanced and improved by incorporating other agents into the basic formulation, such as preservatives, fragrances, pH adjusting agents, and the like. In this regard, the pH of the product is preferably maintained at about 9.2.

In Table VI, one overall preferred formulation for the all natural, shaving foam producing, improved liquid soap of the present invention is provided. As detailed in Table VI, the preferred ingredients are provided, along with the preferred quantity range for each ingredient, detailed as the percent by weight for that ingredient, based upon the weight of the entire composition. By employing compositions consistent with the formulations defined in Table VI, and dispensing the formulations as detailed herein, a foamed shaving mousse is achieved which is capable of providing all of the attributes desired in a smooth, close, comfortable shave, using either blades or electric shavers.

TABLE VI

| Ingredients | Quantity % by Weight |
|---|---|
| Stearic Acid | 1–20 |
| Potassium Cocotte | 4–40 |
| pH Adjusting Agents | 1–10 |
| Enhancing Agents | 0.5–5 |
| Preservatives | 0.1–0.8 |
| Water | Balance to 100% |

In order to further define preferred formulations of the all natural, foam producing, improved liquid soap of the present invention, Table VII is provided to specifically define a more detailed composition. In Table VII the preferred additives and enhancing agents are fully disclosed. In Table VII, each of the ingredients are defined in a preferred quantity range, with the amount provided as a percent by weight, based upon the weight of the entire composition.

TABLE VII

| Ingredients | Quantity % by Weight |
|---|---|
| Stearic Acid | 2–20 |
| Potassium Cocotte Acids | 10–40 |
| Glycerin USP | 0.5–5 |
| Water | 50–90 |
| Citronellol | 0.5–1.0 |
| pH Adjusting Agent | 2–10 |

In carrying out the present invention, an all-natural, liquid foaming soap formulation is produced consistent with the formulations defined above, with the liquid foaming soap formulation being placed in a conventional liquid product holding container. Since pressurization of the composition is not required, the composition is retained in the container at conventional, atmospheric conditions, and any suitable container normally employed for such a liquid product can be used.

Once a suitable quantity of the all natural, liquid foaming soap formulation of the present invention is added to the desired container, the container is closed by mounting a suitable foam producing, dispensing valve or cap to the open portal of the container. In accordance with the present invention, the foam producing dispensing valve or cap mounted to the container within which the improved liquid soap formulation is retained may comprise a wide variety of alternate constructions. However, regardless of the precise configuration employed, a suitable foam producing dispensing valve or cap should be capable of drawing the improved liquid soap into the cap or valve and mixing with air, dispensing the desired foam mousse for use as a shaving cream. Typically, this process includes compressing the improved liquid soap in the valve while infusing air into the soap formulation prior to dispensing the mousse. However, any alternate process can be employed with equal efficacy.

By employing the liquid based foam producing soap and dispensing system of the present invention, a highly desirable foam mousse is achieved and dispensed from the container, having the thickness and density required for providing a smooth comfortable shave. In addition, the shaving mousse produced by the present invention is constructed to provide a low friction, gliding surface over which a conventional razor or electric shaving system is able to comfortably pass while cutting the desired beard or hair fibers.

Due to the inherent, desirable physical characteristics of the foam mousse produced by the improved liquid soap formulation and dispensing system of this invention, a close comfortable shave is realized, with virtually no irritation or cuts being produced. Consequently, even sensitive skin is capable of enjoying a close and comfortable shave without discomfort.

Due to the substantial quantity of water employed in the formulations of this invention, it has been found most desirable to lather the skin first with the foam mousse, and then pat on additional water. In this way, especially when using dry shavers, the application and use of the foam mousse adjusts the skin for the razor. By patting on water, the skin then allows the razor to take full advantage of the slipperiness of the shaving surface, face, or legs.

In an alternate embodiment of the present invention, the desired foam shaving mousse is obtained by employing an all natural liquid soap formed from vegetable oil base which has been split using steam. In the preferred embodiment, the vegetable oil base employed in the present invention is selected from the group consisting of palm kernel oil and coconut oil. For the neutralization of the generated fatty acid, potassium hydroxide has been used. In order to obtain the desired liquid soap formulation, the partially neutralized fatty acids are intermixed with water, heated and agitated. In addition, the pH is adjusted until a pH of between about 9.2 and 10 is achieved. If desired, pH adjusting agents, enchanters, fragrances, and preservatives may be added to the formulation to obtain the final liquid foaming soap product of the present invention. In the preferred embodiment, these additives include aloe vera, rosemary extracts, citric acid, and a blend of natural essential oils.

In the preferred formulation, based upon the weight of the entire composition, the vegetable oil based ingredients ranges between about 30% and 60% of the weight and water makes up about 50% to 90% by weight. These quantities are reduced by the quantity employed for any additive which is desired.

As discussed above, the pH of this embodiment of the liquid foam soap composition is preferably maintained between about 8.8 and 10. More preferably, it has been found that a pH of between about 9.2 and 9.4 is most desirable. It has been found that at a pH level below 9.2, the ingredients may separate and/or may require the inclusion of a preservative. In addition, during the formulation of the liquid foam soap composition, the viscosity of the composition may be adjusted by adding viscosity enhancing agents, in order to assure the production of a thick foam mousse.

Furthermore, as discussed above, the foam generating ingredients are added to water, heated and agitated in order to obtain the desired fully intermixed composition. In this regard, it has been found that raising the temperature of the composition to between about 55° C. and 75° C. provides the desired intermixing, in a manner which is most expeditious.

As discussed above, once a desired composition has been obtained, a suitable quantity of the composition is added to a liquid holding container, with the container being closed by a foam dispensing valve or cap. In this way, the desired, all natural, foam shaving mousse is produced whenever a consumer activates the valve or cap, generating the desired thick, rich, moisture laden foam for application to any skin surface to be shaved.

By employing the teaching of the present invention, all of the desired attributes detailed herein for a foam shaving mousse are realized in a manner which has been previously unattainable. Consequently, the present invention achieves a highly desirable result, enabling the user to obtain a smooth, comfortable shave, using a composition comprising all natural products which are totally devoid of any aerosols or gas producing agents.

It will thus be seen that the object set forth above, among those made apparent from the preceding description, are efficiently attained and, since certain changes may be made in the above product without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in the claims, ingredients or compounds recited in the singular are intended to include compatible mixtures of such ingredients wherever the sense permits.

Having described our invention, what I claim as new and desire to secure by Letters Patent is:

1. A delivery system for enabling the dispensing of a medicinal composition directly to an internal site in a human body, said medicinal composition comprises a therapeutic and anti-viral douche formulation, said delivery system comprising:
   A. a container
      a. constructed for receiving and retaining the medicinal compositions therein,
      b. incorporating an exit portal; and
      c. comprising a thin-walled, flexible construction;
   B. closure means mounted to the portal of the container for securely retaining the medicinal composition; and comprising a cap member affixed to the portal of the container for enabling the medicinal composition in said container to be dispensed directly to the desired internal site in the human body by inserting the elongated tube portion into an orifice of the human body, advancing the tube portion into the cavity associated therewith and enabling the medicinal composition to be dispensed directly to the desired site as pressure is applied to the thin walled, flexible container;
   C. a medicinal composition in the form of a therapeutic and anti-viral douche formulation comprising:
      a. between about 0.01% and 0.08% by weight based upon the weight of the entire composition of citric acid powder;
      b. between about 1% and 5% by weight based upon the weight of the entire composition of one selected from the group consisting of nonoxynol-9 and octoxynol-9;
      c. between about 8% and 12% by weight based upon the weight of the entire composition of glycerine;
      d. between about 0.30% and 2.0% by weight based upon the weight of the entire composition of povidone iodine;
      e. an effective amount of at least one therapeutic agent selected from the group consisting of silver nitrate solutions, silver nanocrystals, and equivalent compounds; and
      f. deionized water forming the balance;
   D. a delivery nozzle or cannula mounted to the closure means and comprising:
      a. an elongated tube portion having an overall length constructed for ease of insertion into an orifice communicating with a cavity of the human body, said overall length being constructed to assure the complete insertion of the tube portion into the cavity without injuring any surrounding tissue; and
      b. at least one aperture formed along the distal end of said elongated tube portion for enabling the douche formulation to be dispensed from the container through the tube portion directly to the desired site; and
      c. an elongated delivery channel formed by the internal diameter of said tube portion and constructed for controlling the delivery pressure produced by squeezing the thin-walled flexible container.

2. The delivery system defined in claim 1, wherein said delivery nozzle or cannula further comprises an enlarged surface formed adjacent the proximal end thereof, for providing a positive stop for said tube member in order to prevent over-insertion of said tube member into the cavity.

3. The delivery system and defined in claim 2, wherein said elongated tube portion is further defined as being formed from flexible material in order to assure ease of use and insertion thereof into the human body for being positioned in the precisely desired location.

4. The delivery system defined in claim 2, wherein said closure means is further defined as comprising one selected from the group consisting of caps and finger-operated dispensing valves, and the delivery nozzle/cannula is further defined as being securely affixed to said closure means in a manner which prevents dislodgement thereof from said closure means.

5. The delivery system defined in claim 4, wherein the elongated tube portion of the delivery nozzle/cannula is further defined as comprising a tapered outer surface with a smaller diameter section being formed at the distal end thereof for further assisting in providing ease of insertion and positioning of the tube member in the desired orifice.

6. The delivery system defined in claim 4, wherein the elongated tube portion of the delivery nozzle/cannula is further defined as comprising a substantially uniform diameter throughout the entire length thereof, with the distal end of said tube portion being smoothly rounded to assure ease of insertion into the desired orifice without injuring any surrounding tissue.

7. The delivery system defined in claim 1, wherein said douche formulation is further defined as comprising:
  A. 0.05% by weight based upon the weight of the entire composition of citric acid powder;
  B. 1.00% by weight based upon the weight of the entire composition of one selected from the group consisting of nonoxynol-9 and octoxylnol-9;
  C. 10% by weight based upon the weight of the entire composition of glycerine;
  D. 0.03% by weight based on the weight of the entire composition of povidone iodine;
  E. a suitable quantity of a fragrance, as needed; and
  F. deionized water forming the balance.

8. A delivery system for enabling the dispensing of medicinal compositions directly to an internal site in a human body, said delivery system comprising:
  A. a container constructed for receiving and retaining the medicinal compositions therein and incorporating an exit portal;
  B. closure means mounted to the portal of the container for securely retaining the medicinal composition; and
  C. a delivery nozzle or cannula mounted to the closure means and comprising:
    a. an elongated tube portion having an overall length constructed for ease of insertion into an orifice communicating with a cavity of the human body, said overall length being constructed to assure the complete insertion of the tube portion into the cavity without injuring any surrounding tissue; and
    b. at least one aperture formed along the distal end of said elongated tube portion for enabling the medicinal composition to be dispensed from the container through the tube portion directly to the desired site; and
  D. a check valve mounted in the container for preventing backflow into the container and comprising a cup member mounted in the portal of the container and said cup member comprises:
    a. a cylindrical shape closed at one end thereof;
    b. an aperture formed in the closed end;
    c. a ball member movably mounted in association with the aperture; and
    d. a disk incorporating a plurality of apertures formed therein, said disk being axially movable in said cup member through a limited distance for controlling the movement of the ball member into and out of the aperture.

9. The delivery system defined in claim 8, wherein said cup member further comprises an inwardly extending lip formed on an inside surface thereof adjacent the disk for controlling the axial movement of the disk.

10. A delivery system for enabling the dispensing of medicinal compositions directly to an internal site in a human body, said delivery system comprising:
  A. a container
    a. constructed for receiving and retaining the medicinal compositions therein,
    b. incorporating an exit portal; and
    c. a thin-walled, flexible construction;
  B. closure means mounted to the portal of the container for securely retaining the medicinal composition; and comprising a cap member affixed to the portal of the container for enabling the medicinal composition in said container to be dispensed directly to the desired internal site in the human body by inserting the elongated tube portion into an orifice of the human body, advancing the tube portion into the cavity associated therewith and enabling the medicinal composition to be dispensed directly to the desired site as pressure is applied to the thin walled, flexible container;
  C. a delivery nozzle or cannula mounted to the closure means and comprising:
    a. an elongated tube portion,
      1. having an overall length constructed for ease of insertion into an orifice communicating with a cavity of the human body, said overall length being constructed to assure the complete insertion of the tube portion into the cavity without injuring any surrounding tissue; and
      2. an elongated delivery channel formed by the internal diameter which is constructed for controlling the delivery pressure produced by squeezing the flexible container, said internal diameter of said elongated tube portion being further defined as ranging between about 0.05 inches and 0.20 inches; and
    b. at least one aperture formed along the distal end of said elongated tube portion for enabling the medicinal composition to be dispensed from the container through the tube portion directly to the desired site.

11. The delivery system defined in claim 10, wherein said elongated tube portion is further defined as comprising an overall length ranging between about 2 inches and 3.5 inches.

12. The delivery system defined in claim 11, wherein the outer diameter of said elongated tube portion is further defined as ranging between about 0.25 inches and 0.35 inches.

13. The delivery system defined in claim 10, wherein the internal diameter of said elongated tube portion is further defined as ranging between about 0.08 inches and 0.156 inches.

* * * * *